United States Patent
Scherer et al.

[11] Patent Number: 5,971,934
[45] Date of Patent: Oct. 26, 1999

[54] NONINVASIVE METHOD AND APPARATUS FOR DETERMINING CARDIAC OUTPUT

[75] Inventors: Peter W. Scherer, Media, Pa.; Gordon R. Neufeld, Shiprock, N.Mex.

[73] Assignee: Trustees of the University of Pennsylvania, Philadelphia, Pa.

[21] Appl. No.: 08/943,555

[22] Filed: Oct. 3, 1997

Related U.S. Application Data

[60] Provisional application No. 60/028,065, Oct. 4, 1996.

[51] Int. Cl.$^6$ .............................. A61B 5/04; A61B 5/02; A61B 5/08
[52] U.S. Cl. ..................... 600/526; 600/484; 600/532; 128/923
[58] Field of Search ..................... 600/484, 526, 600/532, 204.23, 483; 128/920, 923

[56] References Cited

U.S. PATENT DOCUMENTS

| | | |
|---|---|---|
| 3,687,130 | 8/1972 | McCormick . |
| 3,726,270 | 4/1973 | Griffis et al. . |
| 4,169,465 | 10/1979 | Walls et al. . |
| 4,676,253 | 6/1987 | Newman et al. . |
| 4,679,566 | 7/1987 | Tamm . |
| 4,772,559 | 9/1988 | Preti et al. . |
| 4,796,639 | 1/1989 | Snow et al. . |
| 4,949,724 | 8/1990 | Mahutte et al. . |
| 5,086,776 | 2/1992 | Fowler, Jr. et al. . |
| 5,199,438 | 4/1993 | Pearlman . |
| 5,211,177 | 5/1993 | Chesney et al. . |
| 5,316,004 | 5/1994 | Chesney et al. . |
| 5,390,679 | 2/1995 | Martin . |
| 5,400,793 | 3/1995 | Wesseling . |
| 5,423,326 | 6/1995 | Wang et al. . |
| 5,469,859 | 11/1995 | Tsoglin et al. . |
| 5,533,511 | 7/1996 | Kaspari et al. . |
| 5,535,753 | 7/1996 | Petrucelli et al. . |
| 5,584,298 | 12/1996 | Kabal . |
| 5,590,649 | 1/1997 | Caro et al. . |
| 5,647,369 | 7/1997 | Petrucelli et al. . |
| 5,836,300 | 11/1998 | Mault .................................. 600/532 |

OTHER PUBLICATIONS

R.S. Ream, M.D., et al., "Volumetric Capnography in Children," *Anesthesiology*, 82(1):64–73 (Jan. 1995).

J.D. Schwardt et al., "Noninvasive Recovery of Acinar Anatomic Information from $CO_2$ Expirograms," *Annals of Biomedical Engineering*, 22:293–306 (1994).

O. Wendelboe Nielsen et al., "Precision and accuracy of a noninvasive inert gas washin method for determination of cardiac output in men," *J. Appl. Physiol.*, 76(4):1560–1565 (1994).

M.R. Zenger et al., "Measurement of Cardiac Output by Automated Single–Breath Technique, and Comparision with Thermodilution and Fick Methods in Patients with Cardiac Disease," *The American Journal of Cardiology*, 71:105–109 (Jan. 1, 1993).

(List continued on next page.)

*Primary Examiner*—Max Hindenberg
*Assistant Examiner*—Navin Natnithithadha
*Attorney, Agent, or Firm*—Akin, Gump, Strauss, Hauer & Feld, L.L.P.

[57] ABSTRACT

Cardiac output of a test individual is determined in a noninvasive method, by processing $CO_2$ expirogram data obtained from the individual. The method also noninvasively determines pulmonary arterial blood $CO_2$ concentration for the test individual. An apparatus for carrying out this noninvasive method includes a database of computed numerical $CO_2$ expirograms, a device for measuring experimental $CO_2$ expirogram data and means for processing the data sets to determine cardiac output.

28 Claims, 7 Drawing Sheets

OTHER PUBLICATIONS

W.J. Stok et al., "Noninvasive cardiac output measurement by arterial pulse analysis compared with inert gas rebreathing, " *J. Appl. Physiol.*, 74:2687–2693 (1993).

M.S. Schreiner et al., "Microemboli reduce phase III slopes of $CO^2$ and invert phase III slopes of infused $SF_6$, " *Respiration Physiology*, 91:137–154 (1993).

G.R. Neufeld et al., "Modelling steady state pulmonary elimination of He, $Sf^6$ and $CO_2$: Effect of morphometry," *Respiration Physiology*, 88:257–275 (1992).

J.D. Schwardt et al., "Sensitivity of $CO_2$ Washout to Changes in Acinar Structure in a Single–Path Model of Lung Airways," *Annals of Biomedical Engineering*, 19:679–697 (1991).

G.R. Neufeld et al., "Diffusivity, respiratory rate and tidal volume influence inert gas expirograms, " *Respiration Physiology*, 84:31–47 (1991).

J. Conway, "Clinical assessment of cardiac output, " *European Heart Journal*, 11,*Supplement I*:148–150 (1990).

P.W. Scherer et al., "Numerical and experimental study of steady–state $CO_2$ and inert gas washout," *J. Appl. Physiol.*, 64 (3):1022–1029 (1988).

R.L. Stout et al., "Pulmonary blood flow determined by continuous analysis of pulmonary $N_2O$ exchange," *J. Appl. Physiol.*, 38(3):913–918 (May 1975).

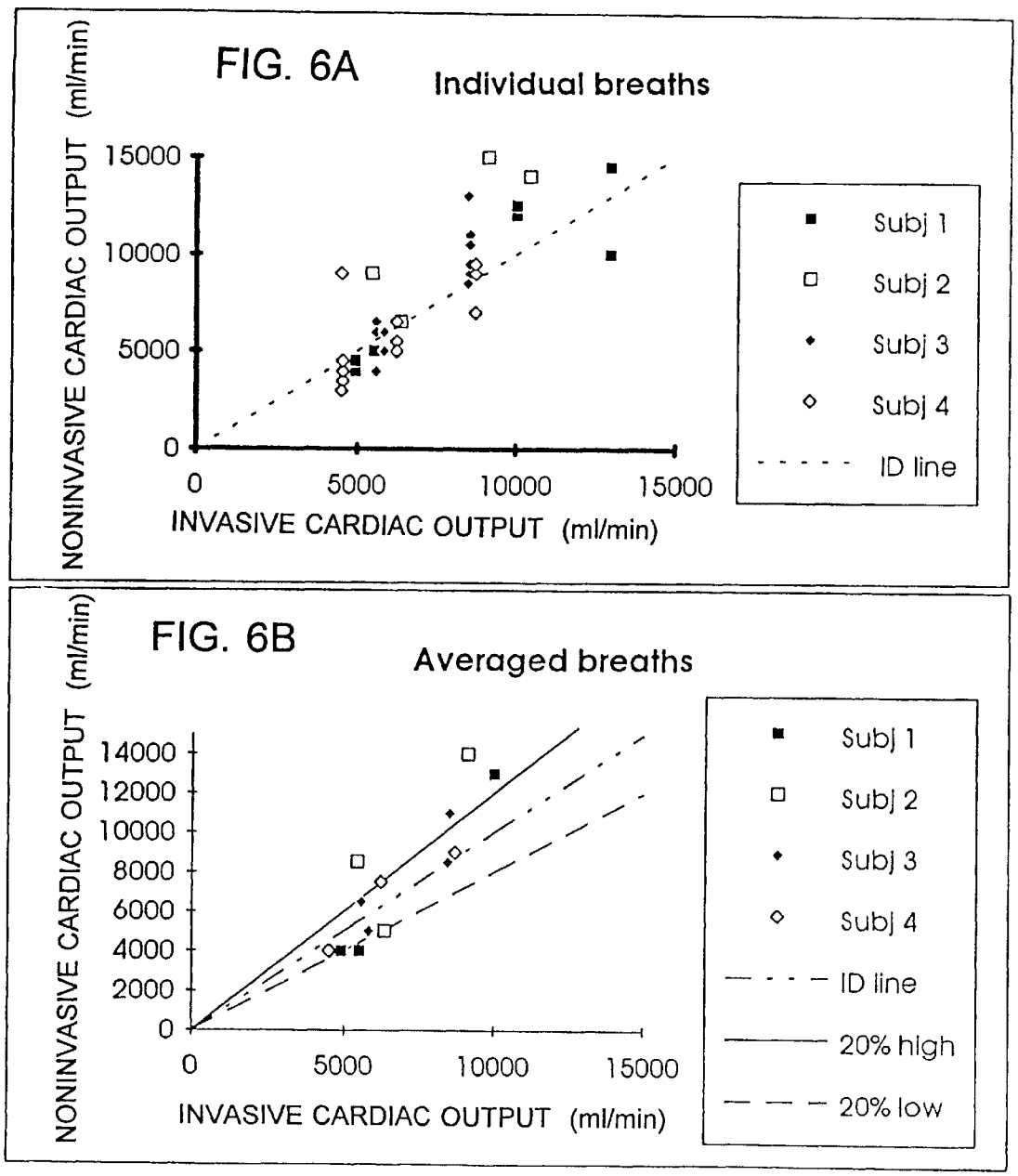

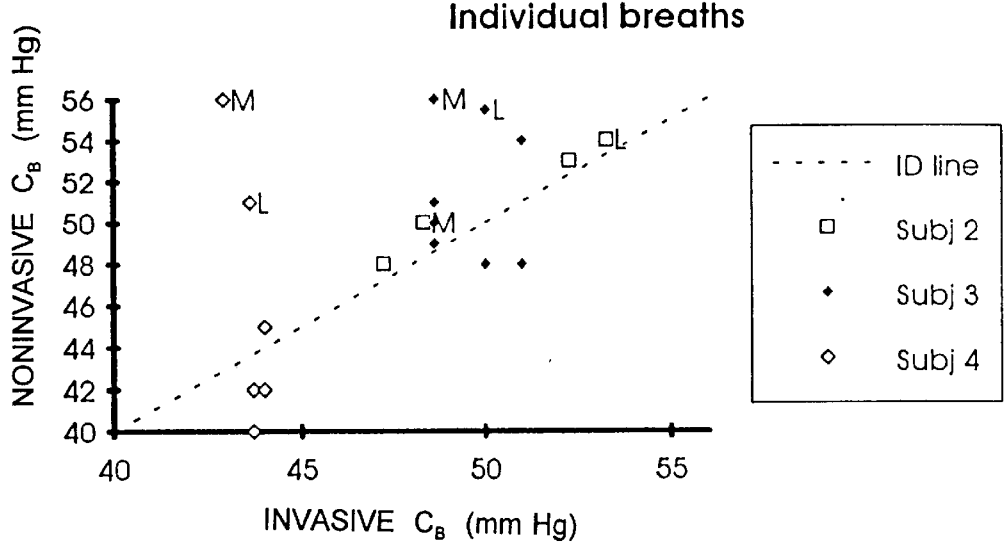
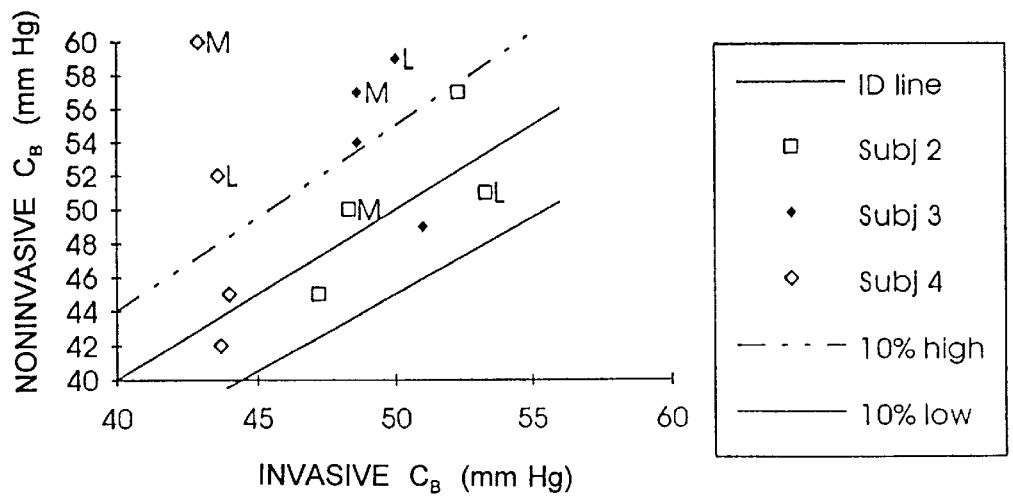

ND APPARATUS
NONINVASIVE METHOD AND APPARATUS FOR DETERMINING CARDIAC OUTPUT

CROSS-REFERENCE TO RELATED APPLICATION

This application claims the benefit of Provisional Application No. 60/028,065 filed Oct. 4, 1996.

BACKGROUND OF THE INVENTION

This invention relates to a noninvasive method and apparatus for determining cardiac output for an individual from $CO_2$ gas expirograms and, more particularly, for determining both cardiac output and pulmonary arterial blood $CO_2$ concentration of an individual.

Cardiac output, sometimes termed total cardiac output, is a well-known term for heart blood flowrate, i.e., the averaged cardiac blood flow per unit of time. Cardiac output for a healthy, adult male human being at rest is about 6000 ml/min, but cardiac output may range from about 1 l/min to about 20 l/min under other conditions (exercise, disease, etc.). Cardiac output is a highly useful measurement in assessing cardiac performance, diagnosing and determining the extent of cardiac and pulmonary disease, and monitoring the effect and effectiveness of treatment protocols involving, e.g., exercise or drugs.

Currently used techniques for determining cardiac output are invasive, i.e., methods requiring skilled personnel in which blood samples are withdrawn for analysis of blood gases, or in which an indicator medium is injected and monitored via blood sampling or catheterization. The dye-dilution technique, for example, requires venous catheterization, with injection proximate to the right atrium, and arterial catheterization with a catheter sufficient for withdrawal of dye-containing blood at a rate of 15–20 ml/min. Thermodilution, a widely used technique, requires right-sided catheterization to the pulmonary artery by a catheter/thermistor, with cold saline being injected near the right atrium to produce a dilution temperature curve useful for accurate determination of cardiac output.

Invasive cardiac output measurement techniques need to be used with great care since they involve a risk of adverse medical consequences if improperly executed. Likewise, the limitations of such invasive techniques are self-evident: they are complex procedures that require trained personnel and controlled conditions, e.g., a clinical environment, and they are not well suited for obtaining repeat measurements from unconfined individuals over extended periods of time. A recent study has raised questions about the safety of right heart catheterizations, i.e. pulmonary artery catheterizations, which are commonly used in invasive cardiac output measurement techniques as described above; see Connors, Jr. et al., *J. Am. Med. Assn.*, (Sept. 18, 1996).

Several noninvasive techniques for determining cardiac output have been reported in the literature, but none has proven to be a simple, easily administered, reliable technique applicable generally to all individuals, i.e., healthy adults and children, as well as diseased and critical care patients; see, e.g., Conway, "Clinical Assessment of Cardiac Output", *Europ. Heart J.* 11:148–150 (1990).

Inert gas and $CO_2$ rebreathing techniques, such as described by Stok et al., "Noninvasive Cardiac Output Measurement by Arterial Pulse Analysis Compared with Inert Gas Rebreathing", *J. Appl. Physiol.*, 74:2687–2693 (1993), tend to raise mixed venous blood $CO_2$ concentration which itself raises cardiac output during the measurement technique. Rebreathing techniques, moreover, are generally not suitable for critically ill patients, since patients are generally required to be cooperative and perform rapid, deep breathing maneuvers.

Stout et al., "Pulmonary Blood Flow Determined by Continuous Analysis of Pulmonary $N_2O$ Exchange", *J. Appl. Physiol.* 38:913–918 (1975), describe a technique for measuring cardiac output by applying an idealized homogeneous lung model to multibreath analyses of soluble inert gas ($N_2O$) and insoluble inert gas ($N_2$ or He) during artificial ventilation of anesthetized dogs breathing a gas mixture containing these components. Nielsen et al., "Precision and Accuracy of a Noninvasive Inert Gas Washing Method for Determination of Cardiac Output in Men", *J. Appl. Physiol.*, 36:1560–1565 (1994), describes the application of the multibreath method of Stout et al. to healthy human beings under controlled ventilation at rest and during exercise, finding that the multibreath method was useful for determining cardiac output under exercise conditions but that an inert gas rebreathing method was more accurate at rest.

Stok et al., "Noninvasive Cardiac Output Measurement by Arterial Pulse Analysis Compared with Inert Gas Rebreathing", *J. Appl. Physiol.*, 74:2687–2693 (1993), describe measurement of changes in cardiac output in healthy adult males by arterial pulse analysis, but this technique requires an initial determination or calibration of absolute cardiac output, e.g., by inert gas rebreathing or other potentially invasive methods.

Zenger et al. "Measurement of Cardiac Output by Automated Single-Breath Technique, and Comparison with Thermodilution and Fick Methods in Patients with Cardiac Disease", *Am. J. Cardiol.*, 71:105–109 (1993), describe measurement of cardiac output from single breath measurements of acetylene gas, used as a tracer gas, but the technique requires controlled inhalation, breath-holding, constant rate exhalation by the individual being tested and administration of a tracer gas not normally present in the lung. This level of cooperation is unworkable with some patients for whom cardiac output measurements are nevertheless highly desirable, e.g., critically ill or unconscious patients.

BRIEF SUMMARY OF THE INVENTION

The present invention is directed to a noninvasive method for determining cardiac output ($\dot{Q}_B$) for an individual which comprises (i) obtaining a data set of multiple $CO_2$ expirograms from a test individual; (ii) determining an airway factor for the data set of multiple $CO_2$ expirograms, to obtain an airway factor characteristic of the test individual; (iii) generating a database of computed numerical $CO_2$ expirograms from an airway numerical model using the airway factor that is characteristic of the test individual and using a range of assumed numerical values for cardiac output that overlaps the expected cardiac output of the test individual; (iv) comparing differences between numerical values of a $CO_2$ expirogram first parameter and an experimental counterpart parameter value from a $CO_2$ expirogram of the test individual and determining, as a function of the numerical cardiac output values, for which cardiac output values such differences are minimized; (v) comparing differences between numerical values of a $CO_2$ expirogram second parameter and an experimental counterpart parameter value from a $CO_2$ expirogram of the test individual and determining, as a function of the numerical cardiac output values, for which cardiac output values such differences are minimized; and (vi) determining a cardiac output for the test individual by cross-comparing the information from (iv) and (v) to obtain a cardiac output value at which the respective differences for the $CO_2$ expirogram first parameter and for the $CO_2$ expirogram second parameter are each minimized, said value being the cardiac output noninvasively determined for the test individual.

Another aspect of the invention is directed to a noninvasive method for determining cardiac output ($\dot{Q}_B$) for an individual which comprises (i) obtaining multiple $CO_2$ expirograms from a test individual wherein such expirograms include Phase III data; (ii) calculating a normalized Phase III slope, NS, as a function of tidal volume for individual $CO_2$ expirograms obtained from the test individual, to generate a population of experimental paired values of normalized Phase III slope as function of tidal volume for such $CO_2$ expirograms; (iii) determining an airway area reduction factor for the population of experimental paired values of normalized slope and tidal volume, to obtain an airway area reduction factor characteristic of the test individual; (iv) generating a population of computed numerical $CO_2$ expirograms with associated paired numerical normalized Phase III slope and $CO_2$ volume exhalation rate values from an airway numerical model using the airway area reduction factor that is characteristic of the test individual and using a range of assumed numerical values for cardiac output, $\dot{Q}_B$, and pulmonary arterial blood $CO_2$ concentration, $c_B$, with ranges that overlap the expected $\dot{Q}_B$ and $c_B$ of the test individual; (v) comparing the differences between numerical normalized Phase III slope values and an experimental normalized Phase III slope value from a $CO_2$ expirogram of the test individual and determining, as a function of the numerical $\dot{Q}_B$ and $c_B$ values, for which paired $\dot{Q}_B$ and $c_B$ values such differences are minimized; (vi) comparing the differences between numerical $CO_2$ volume exhalation rate values and an experimental $CO_2$ volume exhalation rate value from a $CO_2$ expirogram of the test individual and determining, as a function of the numerical $\dot{Q}_B$ and $c_B$ values, for which paired $\dot{Q}_B$ and $c_B$ values such differences are minimized; and (vii) determining a cardiac output for the test individual by cross-comparing the information from (v) and (vi) to obtain a paired value of $\dot{Q}_B$ and $c_B$ at which the respective differences of both normalized Phase III slope and $CO_2$ volume exhalation rate are minimized, the value of cardiac output in said paired value being the cardiac output determined for the test individual.

The invention is also directed to an apparatus for the noninvasive determination of cardiac output for a test individual which comprises (i) a database comprising a population of computed numerical $CO_2$ expirograms for a range of assumed parameter values, including cardiac output, that overlap expected values of these parameters in a population of individuals that includes the test individual; (ii) a device for measuring $CO_2$ gas expirogram data from the test individual; (iii) means for processing data from multiple $CO_2$ expirograms obtained from the test individual to generate a $CO_2$ expirogram data set for the test individual and for calculating an airway factor characteristic of the test individual from such multiple $CO_2$ expirogram data set; (iv) means for computing differences between an experimental value of a first parameter from a $CO_2$ expirogram of the test individual and computed values of the first parameter from numerical $CO_2$ expirograms in the database, whose assumed airway factor is comparable to that of the experimental $CO_2$ expirogram, and for determining for which values of cardiac output such differences are minimized; (v) means for computing differences between an experimental value of a second parameter from a $CO_2$ expirogram of the test individual and computed values of the second parameter values from numerical $CO_2$ expirograms in the database, whose assumed airway factor is comparable to that of the experimental $CO_2$ expirogram, and for determining for which values of cardiac output such differences are minimized; (vi) means for determining a cardiac output for the test individual by cross-comparing the information from (iv) and (v) to obtain a value of cardiac output at which the respective differences of the $CO_2$ expirogram first parameter and the $CO_2$ expirogram second parameter are each minimized; and (vii) means for reporting the value of cardiac output determined in (vi) as the cardiac output of the test individual.

Another aspect of the invention is an apparatus for the noninvasive determination of cardiac output for a test individual which comprises a database comprising a population of computed numerical $CO_2$ expirograms for a range of assumed values for cardiac output, pulmonary arterial blood $CO_2$ concentration, airway area reduction factor, tidal volume and breathing frequency that overlap expected values of these parameters in a population of individuals that includes the test individual; a device for measuring $CO_2$ gas concentration, gas volume, breathing frequency and tidal volume for single breaths from the test individual under steady-state non-rebreathing conditions to generate $CO_2$ expirogram data for the test individual; means for processing data from multiple $CO_2$ expirograms obtained from the test individual to calculate a normalized Phase III slope and tidal volume for each of said multiple $CO_2$ expirograms and to calculate an airway area reduction factor characteristic of the test individual from such multiple $CO_2$ expirogram data; means for computing differences between an experimental normalized Phase III slope from a $CO_2$ expirogram of the test individual and computed values of experimental normalized Phase III slopes in the database, for numerical $CO_2$ expirograms whose assumed airway area reduction factor, tidal volume and breathing frequency are comparable to that of the experimental $CO_2$ expirogram, and for determining for which values of cardiac output and pulmonary arterial blood $CO_2$ concentration such differences are minimized; means for computing differences between an experimental $CO_2$ volume exhalation rate from a $CO_2$ expirogram of the test individual and computed values of experimental $CO_2$ volume exhalation rate values in the database, for numerical $CO_2$ expirograms whose assumed airway area reduction factor, tidal volume and breathing frequency are comparable to that of the experimental $CO_2$ expirogram, and for determining for which values of cardiac output and pulmonary arterial blood $CO_2$ concentration such differences are minimized; means for determining a cardiac output for the test individual by cross-comparing the information from (iv) and (v) to obtain paired values of cardiac output and pulmonary arterial blood $CO_2$ concentration at which the respective differences of both normalized Phase III slope and $CO_2$ volume exhalation rate are minimized; and means for reporting the value of cardiac output determined in (vi) as the cardiac output of the test individual.

BRIEF DESCRIPTION OF THE SEVERAL VIEWS OF THE DRAWINGS

The foregoing summary, as well as the following detailed description of the preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the Drawings:

FIGS. 6A and 6B are plots of invasively-determined values of cardiac output and noninvasively-determined values of cardiac output (calculated according to the inventive method) and obtained from individual breath $CO_2$ expirograms (6A) or for averaged single breath $CO_2$ expirograms (6B), with individual data points for four test individuals being shown, as noted in the legend.

FIGS. 7A and 7B are similar to FIGS. 6A and 6B except that pulmonary arterial (mixed venous) blood $CO_2$ concentrations are plotted as paired invasively-determined and noninvasively determined values for selected individual breath $CO_2$ expirograms (7A) or averaged breath $CO_2$ expirograms (7B) for the three test individuals for whom such data was obtained, as indicated in the legend. The labels "L" and "M" indicate light and moderate exercise, respectively.

DETAILED DESCRIPTION OF THE INVENTION

Figure 1:
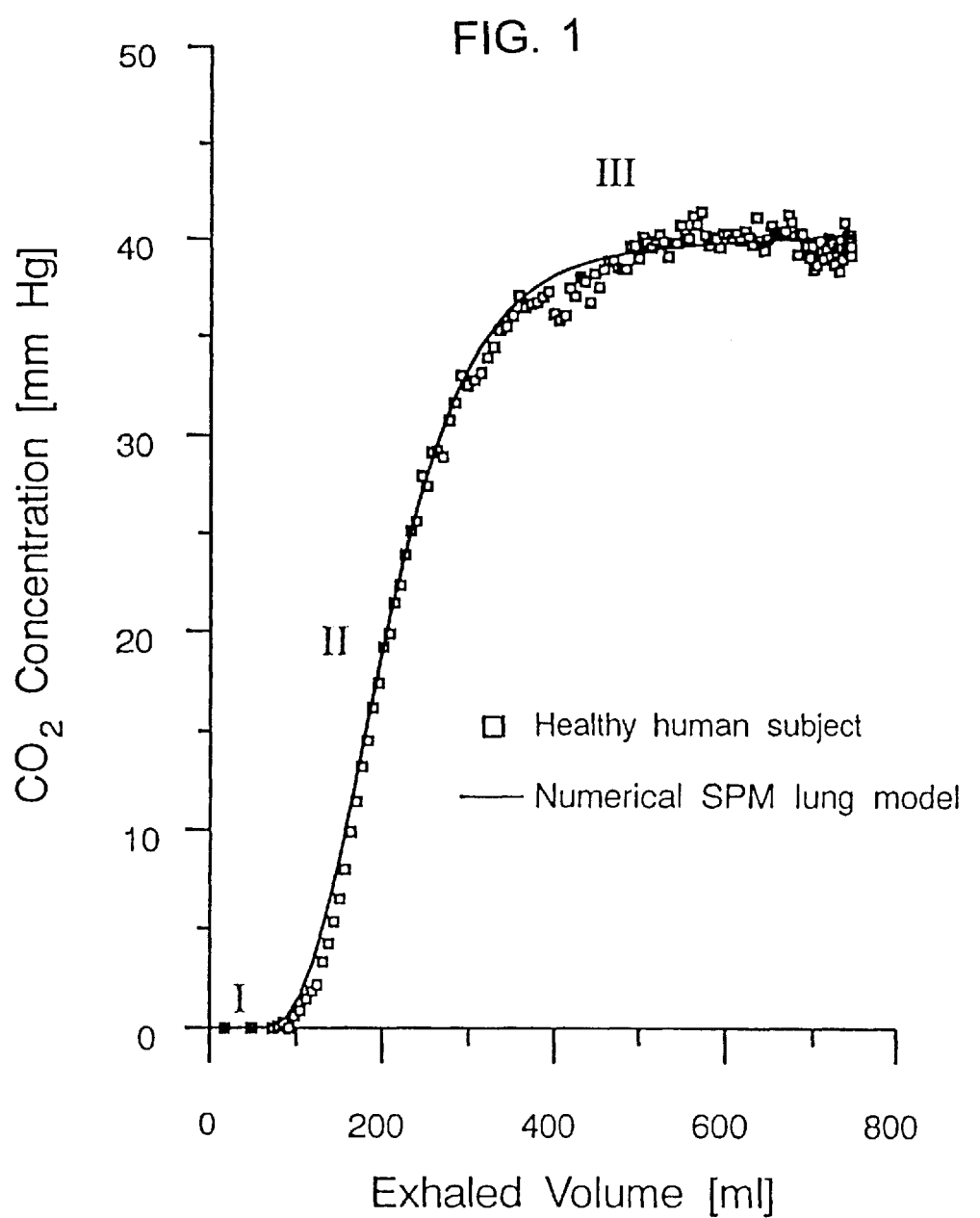
FIG. 1 shows a plot of an experimentally-measured single-breath $CO_2$ expirogram obtained from a healthy human adult individual (FRC=3307 ml, $V_T$=742 ml, f=10.3 breaths per minute), with individual data points being shown for $CO_2$ concentration as a function of exhaled gas volume. The continuous curve indicates a computed numerical $CO_2$ expirogram derived from the single-path model using assumed parameters appropriate for the test individual. The three phases, I, II and III, of the $CO_2$ expirogram curve are also indicated in the Figure.

The method and apparatus of this invention are useful for the noninvasive determination of a test individual's cardiac output; in addition, the individual's pulmonary arterial (mixed venous) blood $CO_2$ concentration may be determined as well. This highly useful information is generated solely from steady-state, single breath $CO_2$ expirogram data that is experimentally obtained from the test individual, using conventional methodology to obtain the $CO_2$ expirogram data. A test individual's cardiac output and pulmonary arterial blood $CO_2$ concentration are obtained in this invention using only measurements of single breath $CO_2$ expirogram data, without the need for measuring experimental values for other parameters defining the test individual's respiratory or cardiac functioning. In particular, invasive procedures often used in the prior art to obtain parameter values used for determining cardiac output, e.g., measurement procedures involving catheterization or made via telemetry from a pacemaker or other implanted device, are unnecessary for determining a subject's cardiac output according to this invention.

The method of this invention is based on the discovery that cardiac output for a test individual, and pulmonary arterial (mixed venous) blood $CO_2$ concentration (gas pressure) as well, may be determined by comparing each of two measured parameters derived from the individual's $CO_2$ expirogram data, i.e., $CO_2$ volume excreted per unit time and normalized Phase III slope, against simulated, numerical values of the same parameters calculated from a mathematical model that uses a factor characteristic of the test individual's $CO_2$ expirogram data. The comparison yields (absolute) difference data for each parameter as a function of paired numerical values, from the mathematical model, of cardiac output and of pulmonary arterial blood $CO_2$ concentration that are associated with each of the numerically calculated parameter values. A single value of cardiac output and a single value of pulmonary arterial blood $CO_2$ concentration, representing values of these two parameters determined for the test individual, are determined by cross comparing the respective regions of minimized absolute differences of $CO_2$ volume excreted per unit time and of normalized Phase III slope. The present invention exploits the unexpected finding that these regions of minimized absolute differences are situated in an orthogonal relationship, when compared as functions of cardiac output and pulmonary arterial blood $CO_2$ concentration. These and other aspects of the invention are described below in more detail.

The noninvasive method of this invention is superior to prior art noninvasive cardiac output techniques in numerous respects, particularly because of its operational simplicity and versatility.

The noninvasive method of this invention is useful with adults and children and with healthy, diseased and critical care individuals. The invention can be adapted to veterinary applications as well, e.g., determining cardiac output of mammals such as horses.

The method of this invention does not require the use of highly trained personnel to administer the procedure. Personnel with knowledge of the simple breathing maneuvers or protocols used in this invention can be taught to coach the test subjects. The method uses multiple $CO_2$ expirograms that are obtained from the test individual under a variety of steady-state breathing conditions, e.g., normal breathing, rapid breathing, shallow breathing, shallow-rapid breathing, deep breathing, slow breathing, slow-deep breathing or the like, while at rest or under exercise conditions, e.g., light, moderate and/or heavy exercise conditions. The single breath $CO_2$ expirograms are typically obtained from the test individual under several of these breathing conditions, at steady-state, to provide multiple single breath $CO_2$ expirograms that represent a range of different tidal volumes for the test individual.

The method of this invention does not require active cooperation from the test subject and may be used with patients who are anesthetized, on a respirator or other mechanical ventilation equipment, or who are sleeping or otherwise unconscious. In fact, the method of this invention is particularly suited for use with patients on mechanical ventilation since such equipment may easily be adjusted to specific breathing parameters (e.g., frequencies and/or tidal volumes) for generation of multiple single breath $CO_2$ expirograms from the individual under varied breathing conditions.

One advantage of this invention over prior art techniques such as inert gas rebreathing techniques is that the method does not alter the parameters being measured. For example, pulmonary arterial (mixed venous) blood $CO_2$ concentration and, likewise, the heart rate and cardiac output, are not altered from normal values by the action of carrying out the method of this invention. This aspect is very important for some patients, e.g., critically ill patients, when respiratory function may be impaired and may be adversely affected by a rebreathing maneuver.

The present invention utilizes data from $CO_2$ expirograms that are obtained experimentally or empirically from the test individual for whom a determination of cardiac output is desired. Single breath expirograms are measurements of an individual's expired or exhaled $CO_2$ concentration as a function of exhaled gas volume in the exhalation period of a single breath. Such single breath expirograms are generally obtained by measurements of total exhaled gas "at the mouth", which should be understood to mean at the mouth (with the nose clipped), or at the mouth and nose combined, or at the nose (with mouth closed), or, if the subject is mechanically ventilated, at the end of an endotracheal tube.

The single breath expirograms used in this invention are obtained from the test individual under normal breathing conditions, i.e., while breathing ambient air under steady-state conditions, as opposed to rebreathing all or a portion of the exhaled gas. The term "ambient air" refers to air normally surrounding and breathed by a test individual; such ambient air does not contain additional added components, e.g., tracer gases, not normally found in air. The term "ambient air" is also intended to cover individuals ventilated mechanically with a respirator or the like, including individuals receiving supplementary oxygen or anesthetic gases.

The present invention utilizes data from several single breath $CO_2$ expirograms (such $CO_2$ expirogram data should include $CO_2$ concentration as a function of the volume of exhaled gas, the volume of exhaled gas (tidal volume, $V_T$) and the breathing frequency (f), or combinations of these parameters that yield the same information) to determine cardiac output and, optionally and preferably, pulmonary arterial blood $CO_2$ concentration. No other gas concentrations besides $CO_2$ in the exhaled breaths of the test individual are required to be measured. Likewise, no other physiological or physical measurements are required to be obtained from the test individual.

Several $CO_2$ expirograms are obtained from the test individual in this invention to generate multiple $CO_2$ expirograms, preferably at least ten individual breath $CO_2$ expirograms. These are also preferably obtained at several different tidal volumes by obtaining $CO_2$ expirograms from the test individual at different breathing conditions, as described earlier. However, the multiple $CO_2$ expirogram may include several individual breath $CO_2$ expirograms obtained at similar breathing conditions, provided that the multiple $CO_2$ expirograms comprise data for more than one tidal volume.

A $CO_2$ expirogram is a well-known measurement of one aspect of an individual's respiratory function. Measurement of a $CO_2$ expirogram is relatively straight-forward. The subject inhales ambient air, and the $CO_2$ concentration and cumulative exhaled gas volume are measured and recorded during exhalation. A $CO_2$ expirogram typically represents data from a single breath, but measurements of multiple $CO_2$ expirograms may be obtained under similar conditions and then averaged to provide a representative $CO_2$ expirogram that is more likely to be free of experimental "noise".

A $CO_2$ expirogram may also be called a "capnogram" or "a $CO_2$ washout curve" or "volumetric capnogram." A $CO_2$ expirogram is a plot of $CO_2$ gas concentration versus exhaled, i.e., expired, cumulative gas volume. An example of a $CO_2$ expirogram for a healthy adult male human being (functional residual capacity (FRC)=3307 ml, tidal volume ($V_T$)=742 ml, f=10.3 breaths per minute) is shown by the data points plotted in FIG. 1. The plot generated in a $CO_2$ expirogram is customarily divided into three phases, such as shown in FIG. 1. Phase I is the washout of the uppermost conducting airways and is almost completely free of $CO_2$. Phase II is the rapidly rising portion of the $CO_2$ washout curve. Phase III, also known as the "alveolar plateau," represents gas contained in the pulmonary acini or peripheral alveolated airways. Phase III contains most of the exhaled $CO_2$, and this portion of the $CO_2$ washout curve is usually characterized by a relatively linear increase in $CO_2$ concentration versus cumulative exhaled volume. The expired tidal volume ($V_T$) is measured as the absolute volume of gas inhaled (inspired) and exhaled (expired) in one respiratory cycle, and tidal volume may be expressed either as the absolute volume (ml) or as volume per kilogram of bodyweight (ml/kg), the former being used in FIG. 1.

The present invention utilizes single breath $CO_2$ expirograms for steady-state breathing, in contrast to prior art washout methodologies that are based on analyses of non-steady-state breathing, e.g., inert gas rebreathing or the like. In steady-state breathing, steady-state ventilation is used to equilibrate the lung at the particular breathing condition selected, but in non-steady-state breathing maneuvers, the gas concentrations change throughout the test breath and throughout each subsequent breath. The steady-state breathing used in carrying out this invention may be characterized as a natural, equilibrated breathing or ventilation condition, in contrast to non-steady-state breathing which may be characterized as an artificially induced condition.

The procedures and techniques for obtaining $CO_2$ gas expirograms are well known to those skilled in the medical arts, particularly, in anesthesiology, and have been widely reported in the literature. $CO_2$ expirograms may be routinely obtained by personnel without a high level of specialized training, using equipment that is readily available from commercial medical equipment sources. Anesthesiologists routinely record $CO_2$ expirograms as a means of monitoring changes in a subject's respiratory function. However, $CO_2$ expirograms have otherwise been of limited utility except for the measurement of end tidal $CO_2$. In recent years, researchers have utilized data from $CO_2$ expirogramns as a means of characterizing pulmonary structure and function in healthy subjects and in subjects with pulmonary disease; see, e.g., Schwardt et al., "Noninvasive Recovery of Acinar Anatomic Information from $CO_2$ Expirograms," *Ann. Biomed. Eng.*, 22:293–306 (1994); and Schwardt et al., "Sensitivity of $CO_2$ Washout to Changes in Acinar Structure in a Single-Path Model of Lung Airways," *Ann. Biomed. Eng.*, 19:679–697 (1991).

Several of these reports, including those just referenced, have utilized a mathematical single-path model (SPM) of the human lung airways that is based on the solution of the airway convection-diffusion equation. The single-path model has also been referred to as a symmetric single-path trumpet bell model and is discussed in more detail below. The single-path model has been shown to simulate mathematically $CO_2$ expirograms that are in agreement with experimental $CO_2$ expirogram data generated under a variety of conditions. The single-path model utilized in these research reports incorporated anatomic dimensions for a standard healthy lung model, such as that of Weibel's symmetric Model A which specifies airway length, diameter and number of alveoli per generation for 23 generations (z) of dichotomous branching airways. The conducting airways are represented by generations z=0–16, and the alveolated airways are generations z=17–23.

The Weibel Model A is the most often used model for a standard healthy lung; see Weibel, "Morphometry of the Human Lung," Springer-Verlag, Berlin (1963). However, other airway anatomic models such as those of Haefeli-Bleuer & Weibel and Hansen & Ampaya are likewise well known and these other morphometric models of the human lung may be used in place of Weibel Model A in the single-path model; see, e.g., Haefeli-Bleuer & Weibel, "Morphometry of the Human Pulmonary Acinus", *Anat. Rec.* 220:401–414 (1988); and Hansen & Ampaya, "Human Airspace Shapes, Sizes, Areas and Volumes," *J. Appl. Physiol.* 38:990–995 (1975). These models typically differ in the rate of expansion of cross-sectioned area of the proximal alveolated acinar airways. The effect of using these different morphometric models in numerical $CO_2$ expirograms mathematically generated from a single-path convection-diffusion airway model and their respective fits to experimentally generated $CO_2$ expirogram data are well known; see, e.g., Neufeld et al., "Modelling Steady State Pulmonary Elimination of He, $SF_6$ and $CO_2$: Effect of Morphometry," *Respir. Physiol.* 88:257–275 (1992), which contains a detailed discussion of a study using these morphometric models. Morphometric lung models for children and for small and large animals may also be used in the single-path model, if desired. For purposes of this invention, the selection of a specific morphometric model is not critical, provided that once a morphometric model is selected, that model is used consistently for all aspects and steps of the claimed invention. The Neufeld et al. (1992) report concluded that normalized slopes calculated at the mouth by a steady-state single-path diffusion convection model of pulmonary gas ($CO_2$) transport with a blood source term agree reasonably well both qualitatively and quantitatively with the experimental data.

Applications of the single-path model to the human respiratory system and correlation of simulated data generated from the single-path model with experimental data obtained from $CO_2$ and other gas expirograms have been extensively described and discussed in the literature; see, e.g., Ream et al., "Volumetric Capnography in Children," *Anesthesiology*, 82:64–73 (January 1995); Schwardt et al., "Noninvasive Recovery of Acinar Anatomic Information from $CO_2$ Expirograms," *Ann. Biomed. Eng.*, 22:293–306 (1994); Schwardt et al., "Sensitivity of $CO_2$ Washout to Changes in Acinar Structure in a Single-Path Model of Lung Airways," *Ann. Biomed. Eng.*, 19:679–697 (1991); Neufeld et al., "Diffusivity, Respiratory Rate and Tidal Volume Influence Inert Gas Expirograms," *Resp. Physiol.*, 84:31–47 (1991); and Scherer et al., "Numerical and Experimental Study of Steady-State $CO_2$ and Inert Gas Washout," *J. Appl. Physiol.*, 64:1022–1029 (1988).

The single-path trumpet bell numerical model of steady-state pulmonary $CO_2$ gas exchange is based on a numerical solution of the classic single-path airway convection-diffusion equation. This single-path numerical model was originally developed to study the washout of $CO_2$ gas undergoing diffusive transfer from the blood into alveolar air. The studies described above confirm the good correspondence between normalized Phase III slopes determined experimentally from $CO_2$ expirograms obtained from test individuals and a numerically determined normalized Phase III slope obtained from solution of the single-path mathematical model, using a morphometric model of the human lung, e.g., Weibel Model A.

The single-path model of airway convection and diffusion in the human respiratory system may be represented by the following equation (1):

$$(V + V_A)\frac{\partial C}{\partial t} + \dot{Q}\frac{\partial C}{\partial z} = \frac{\partial}{\partial z}\left(\frac{DA}{l}\frac{\partial C}{\partial z}\right) + S(z, t) \quad (1)$$

The nomenclature and symbols used in the airway convection-diffusion equation shown above and in literature discussions of this equation are defined in the Table below.

TABLE

Nomenclature $A = A(z)$ = total airway cross sectional area of generation z [cm$^2$]
$c(z,t)$ = $CO_2$ concentration in generation z at time t [cm$^3$$CO_2$/cm$^3$, dimensionless]
$c_B$ = $CO_2$ concentration in equilibrium with the pulmonary arterial blood [mm Hg]
$D = D_{mol}$ = molecular diffusivity [cm$^2$/sec]
$f$ = breathing frequency [breaths per minute (bpm)]
FRC = functional residual lung capacity [cm$^3$]
$N_A$ = number of alveoli in generation z [dimensionless]
$N_T$ = total number of alveoli in Weibel lung [dimensionless]
$P_{A_{CO2}}$ = alveolar CO2 concentration [mm Hg]
$\dot{Q}(z,t)$ = volume flowrate through airways in generation z at time t [cm$^3$/sec]
$\dot{Q}_B$ = total cardiac output [cm$^3$/sec]
SPM = single path model
$S(z,t)$ = alveolar capillary $CO_2$ emitted from blood in generation z at time t [cm$^3$/sec]
$t$ = time [seconds]
$V = V(z)$ = airway volume of generation z [cm$^3$]
$V_A(z,t)$ = alveolar volume of generation z at time t [cm$^3$]

TABLE-continued

Nomenclature $V_{A,T}$ = total alveolar volume in lung at beginning of inspiration [cm$^3$]
$V_{CO_2}$ = CO2 volume exhalation rate [cm3/min]
$V_T$ = tidal volume [ml]
z = generational coordinate [dimensionless]
$\Delta Z$ = finite increment in generational coordinate [dimensionless]
$\beta$ = airway area reduction factor [dimensionless]

The single-path airway model may be used to perform computer simulations, in which each simulation involves repeated explicit finite different solutions to the airway convection-diffusion equation at positions throughout the airway path for each increment in time.

The last term on the right in the equation shown above is the blood source term that represents $CO_2$ evolution from the blood into the lung airspace according to the local blood flow distribution. The blood source term, S(z,t), is a distributed source term for the elimination of gases from mixed venous blood and is distributed among the generations of alveolated airways in proportion to the number of alveoli in each airway generation (z). A preferred definition of the blood source term for $CO_2$ as the gas is given as Equation (2) at page 682 of Schwardt et al., "Sensitivity of $CO_2$ Washout to Changes in Acinar Structure in a Single-Path Model of Lung Airways," Ann. Biomed. Eng., 19:679–697 (1991). Other definitions for the blood source term, however, may be used in Equation (1) without adversely affecting the method of this invention.

The numerical single-path model may be used to generate $CO_2$ expirograms when assumed or hypothetical values for the input parameters are supplied. The parameter values for a standard healthy adult human being are typically used for such assumed or hypothetical values; see, e.g., Schwardt et al. (1994) and (1991), op. cit. Adjustable parameters and physiologic variables in the single-path model include tidal volume ($V_T$), breathing frequency (f), total cardiac output ($\dot{Q}_B$), pulmonary arterial (mixed venous) blood $CO_2$ concentration ($c_B$), functional residual lung capacity (FRC), pulmonary blood flow distribution (($N_A/N_T)\dot{Q}_B$), total alveoli volume at the beginning of inspiration ($V_{A,T}$), airway cross-sectional area (A(z)), and gas-phase molecular diffusivity ($D_{mol}$).

Standard values of physiologic and structural parameters may be chosen based on normal breathing in a healthy adult male. Such standard values, with normal breathing being simulated with a symmetric sinusoidal air-flow pattern at the mouth, are as follows: $V_T$=750 ml; f=12 breaths/min; $\dot{Q}_B$=6.6 l/min; and $c_B$=48 mm mercury (Hg), in a single-path model using an FRC=2500 ml. Standard blood flow distribution may be based on the values of $N_A$ and $N_T$ from the Weibel Model A. The standard value for $V_{A,T}$=1440 ml may be determined as the difference between the FRC and the total airway volume of the scaled Weibel Model A geometry. For the single-path model, A(z) may be determined according to the scaled Weibel geometry, and $D_{mol}$=0.17 cm$^2$/sec, which is the value for $CO_2$ in alveoli air. The above-noted parameter values for the $V_T$ and $\dot{Q}_B$ are consistent with normal breathing in a healthy adult male at rest and are representative values. For an adult population, including healthy and diseased individuals, exemplary ranges for these parameters (for individuals at rest and during moderate exercise) are as follows. Tidal volume ($V_T$) may range from about 200 to about 2500 ml. Breathing frequency (f) may range from about 4 to about 40 breaths per minute. Total cardiac output ($\dot{Q}_B$) may range from about 1 to about 20 l/min.

Representative ranges for other parameters in the single-path model, for healthy and diseased adults, are as follows. Functional residual capacity (FRC) may range from about 1500 to about 4500 ml. Alveolar volume ($V_{A,T}$) may range from about 400 to about 3500 ml. Pulmonary arterial blood $CO_2$ concentration ($c_B$) may range from about 30 to about 80 mm Hg, and this range of $c_B$ represents conditions of hypocapnia and hypercapnia for healthy subjects during exercise and in patients suffering from severe emphysema.

The airway area reduction factor is a multiplier constant applied to the single-path model airway cross-sectioned in generations 17–23 (the alveolated airways). The airway (acinar) area reduction factor $\beta$ is used to determine the total airway cross-section (A(z)) by multiplying the factor $\beta$ by the areas in generations 17–23 from the Weibel Model A which specifies airway length, diameter and number of alveoli per generation for 23 generations of dichotomous branching airways. The airway cross-section A(z) in the single-path model is the summed cross-section of all branches in generation z.

The acinar area reduction factor $\beta$ is a dimensionless factor which is used in this invention as a factor that best represents the simulation of the single-path model to experimental $CO_2$ expirogram data obtained from a test individual. The single-path model for a standard healthy adult male has an airway (acinar) area reduction factor $\beta$ equal to 1.0. The single-path model applied to a population of individuals will generally result in a range of acinar area reduction factors of from about 0.2 to 2.0; this range covers both healthy individuals and individuals suffering from pulmonary disease.

Figure 3:
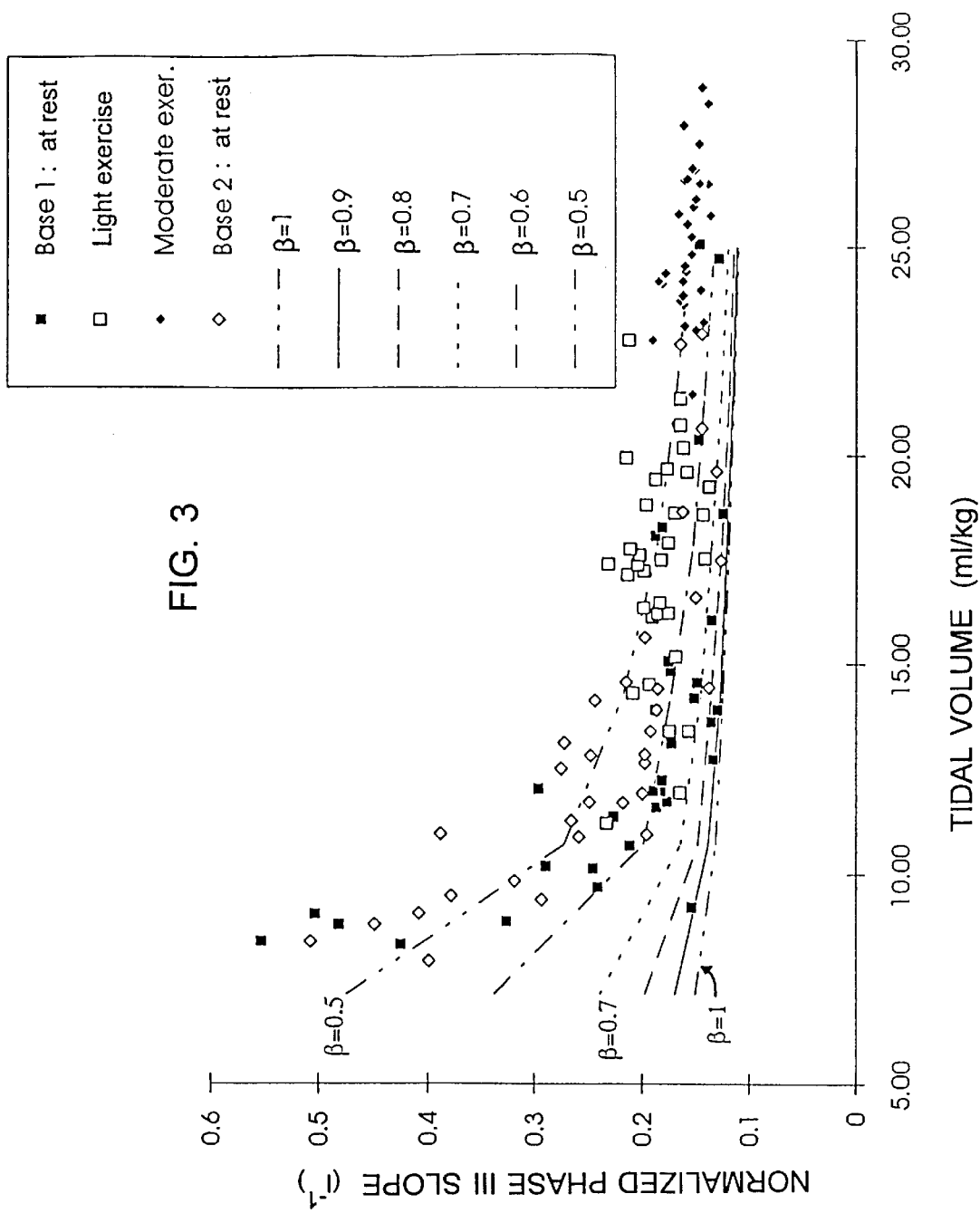
FIG. 3 depicts a plot of normalized Phase III slope and associated tidal volume data for a single test individual. The data points indicate such values obtained from $CO_2$ expirograms for a test individual evaluated while breathing steady-state at rest and under light and moderate exercise conditions, as shown in the legend. The curves shown in the plot are for normalized Phase III slope and tidal volume values calculated from a single-path mathematical model at six values for airway area resistance factor β, as shown in the legend.

Determination of an airway (acinar) area reduction factor $\beta$ for a given individual may be readily accomplished using $CO_2$ expirogram data, e.g., such as shown in FIG. 1. In particular, $CO_2$ expirogram data experimentally obtained from an individual, i.e., the multiple $CO_2$ expirograms, may be used to generate a plot of normalized Phase III slopes versus tidal volumes. Such a plot is shown in FIG. 3, which is discussed in more detail in connection with the Example below. The Phase III slopes from the $CO_2$ expirograms are normalized by scaling the Phase III slope by its mixed expired $CO_2$ concentration over the entire expirogram tidal volume. Normalization in effect converts each $CO_2$ expirogram normalized factor to represent the factor per unit $CO_2$ gas excretion. The normalized Phase III slope may be determined from a $CO_2$ expirogram as the slope of the Phase III portion of the $CO_2$ concentration versus exhaled volume curve, normalized by dividing the exhaled $CO_2$ concentration by the mixed expired $CO_2$ concentration of the exhaled volume (i.e., the latter represented by the area under the $CO_2$ concentration versus exhaled volume curve).

The plot of experimental values of normalized Phase III slopes as a function of tidal volume thus generated may be compared to other numerically generated curves obtained by generating a family of simulated normalized Phase III slope versus tidal volume curves using airway area reduction factors ranging from, e.g., 0.2 to 2.0 in increments of 0.1 or 0.2 with a single-path model having the standard values of physiologic and structural parameters noted above for a healthy adult male. Such curves are shown in the plot shown in FIG. 3, for a range of airway area reduction factors of from 0.5 to 1.0. The determination of an experimental airway area reduction factor $\beta$ in this manner, by fitting experimentally-obtained normalized Phase III slope versus tidal volume data to a numerically-calculated airway area reduction factor curve, is readily understood by one skilled in the art as evidenced by the disclosures in the Schwardt et al. (1994) and (1991) references cited above.

For purposes of the present invention, it should be noted that consistency in the selection of parameter definitions and assumed values and in their use in the method of the invention is more important than the specific parameter definition or absolute value selected. The method of this invention is based on comparisons that are made between experimental and numerical parameter values, so it is important, e.g., that the single path model utilized in the invention be applied uniformly and consistently in all aspects of the inventive method. Likewise, a parameter, such as the definition of Phase III of a $CO_2$ expirogram, used for both experimental and numerically generated $CO_2$ expirograms should be defined in the same manner for each: in the Example described below, the beginning of Phase III was defined as the volume equal to 1.8 times $V_{Daw}$, (the volume of anatomic dead space of the airways (calculated by the method of Langley et al., "Ventilatory Consequences of Unilateral Pulmonary Artery Occlusion," *Colloques. Inst. Natl. Santé Réch. Méd.*, 51:209–212 (1975); and the end of Phase III was defined as exhaled volume at 95% of $V_T$, tidal volume.

The noninvasive method of this invention determines cardiac output and, also, pulmonary arterial blood $CO_2$ concentration for an individual in a technique based on separate comparisons of an experimental normalized Phase III slope and an experimental $CO_2$ volume exhalation rate from the test individual against computed values of these same two parameters calculated from the single-path model using the experimental airway reduction factor β that is characteristic of the test individual. The absolute differences for each of these two parameters between the value found experimentally from the test individual and counterpart values computed using the single-path model are minimized, as functions of paired numerical values of cardiac output and pulmonary arterial blood $CO_2$ concentration.

The experimental values for an individual's normalized Phase III slope and for $CO_2$ volume exhalation rate used in the comparison of numerically calculated values of these parameters and an experimental value are obtained from one or more $CO_2$ expirograms for the test individual. The above-mentioned "one or more $CO_2$ expirograms" are generally a subset selected (as described below) from among the multiple experimental $CO_2$ expirograms obtained from the test individual. The normalized Phase III slope is calculated in the same manner as described above, but is a single representative value (or averaged value), rather than a population of normalized Phase III slope values such as was used to generate the airway area reduction factor characteristic of the test individual.

The second parameter, $CO_2$ volume exhalation rate, may also be determined from the above-mentioned "one or more $CO_2$ expirograms". The $CO_2$ volume exhalation rate may be calculated from the area under the $CO_2$ expirogram curve multiplied by the breathing frequency used during the generation of such $CO_2$ expirogram. Alternatively, the $CO_2$ volume exhalation rate may also be determined from the tidal volume (corresponding to the total exhaled volume in the $CO_2$ expirogram) multiplied by the breathing frequency and multiplied by the mixed expired $CO_2$ concentration (i.e., the area under the $CO_2$ expirogram curve).

These two parameters, normalized Phase III slope and $CO_2$ volume exhalation rate, may be determined from a single experimental $CO_2$ expirogram from the test individual, where such $CO_2$ expirogram is representative of the multiple $CO_2$ expirogram obtained from the test individual. Alternatively, these two parameters may be determined or obtained from two or more experimental $CO_2$ expirograms from the test individual, either as average values or mean values obtained from such multiple experimental $CO_2$ expirograms. These two parameter values are preferably obtained from $CO_2$ expirograms obtained from the test individual under steady-state breathing conditions with the individual at rest. When the two parameters are determined by combining data from two or more $CO_2$ expirograms, it is preferable that the expirograms being combined are those obtained under similar breathing conditions, i.e., similar tidal volume and breathing frequency. This approach is preferred since the resulting experimental values of $CO_2$ volume exhalation rate and normalized Phase III slope are more likely to be representative values in which normal experimental variation (experimental "noise") is minimized.

In this invention, a population of computed numerical $CO_2$ expirograms is generated using the single-path model with a numerical airway area reduction factor that is essentially the same as the experimental airway area reduction factor that is characteristic of the test individual. These computed numerical $CO_2$ expirograms are preferably generated at the same values of tidal volume and breathing frequency applicable to the experimental normalized Phase III slope and $CO_2$ volume exhalation rate being utilized for the test individual, i.e., applicable to the $CO_2$ expirograms used to obtain such parameter values. The population of computed numerical $CO_2$ expirograms that is generated is used to obtain computed paired values of normalized Phase III slope and $CO_2$ volume exhalation rate for each of the numerical expirograms. This population of computed numerical $CO_2$ expirograms, each with associated paired numerical values of normalized Phase III slope and $CO_2$ volume exhalation rate, is used as the basis for comparison with the experimental normalized Phase III slope and $CO_2$ volume exhalation rate determined for the test individual.

It is possible and preferable to create a database comprising populations of computed numerical expirograms for a range of assumed numerical airway area reduction factors, e.g., β values within a range of 0.2 to 2.0, and for a range of tidal volumes and breathing frequencies, where such ranges overlap the anticipated experimental counterpart values of these parameters in a population of individuals that includes the test individual. The advantage of this approach is that the population of computed numerical $CO_2$ expirograms with associated paired numerical normalized Phase III slope and $CO_2$ volume exhalation rate values is available in a reference database, e.g., stored in a computer, for comparison with the experimental normalized Phase III slope and $CO_2$ volume exhalation rate determined from the experimental $CO_2$ expirogram data of the test individual, at the desired airway reduction factor value and tidal volume and breathing frequency values for such experimental $CO_2$ expirogram.

The population of computed numerical $CO_2$ expirograms is generated from the single-path numerical model using a range of assumed values for cardiac output and for pulmonary arterial blood $CO_2$ concentration, with the ranges selected for these two parameters being ranges that overlap the expected cardiac output and pulmonary arterial $CO_2$ concentration of a population of individuals that includes the test individual being evaluated. This may be accomplished by means of a computer. Using essentially the same value of β, the airway area reduction factor determined experimentally for the test individual, and using essentially the same tidal volume and breathing frequency used for the test individual's experimental $CO_2$ expirogram and associated normalized Phase III slope and experimental $CO_2$ volume exhalation rate, the single-path model provides a population of numerical $CO_2$ expirograms for the assumed ranges of values for cardiac output and for pulmonary arterial blood $CO_2$ concentration. For every set of paired values of cardiac output and pulmonary arterial blood $CO_2$ concentration, a numerical $CO_2$ expirogram curve is generated by the single-path model with computed paired values for normalized Phase III slope and for $CO_2$ volume exhalation rate.

A comparison may then be made between the experimental normalized Phase III slope value from the test individual and each of the numerical normalized Phase III slope values for the computed $CO_2$ expirograms with associated paired values of cardiac output and pulmonary arterial blood $CO_2$ concentration. The absolute differences between the experimental normalized Phase III slope and each of the computed normalized Phase III slope values may be analyzed by plotting the data on a three-dimensional graph to obtain a contour map with the numerical values of cardiac output and of pulmonary arterial blood $CO_2$ concentration being plotted on the X and Y axis of a three-dimensional graph and the absolute differences between the experimental value of normalized Phase III slope and each of the calculated values of normalized Phase III slope may be plotted on the Z axis to obtain a contour map, such as is shown in FIG. 4B. The contour map typically exhibits a "valley" of minimal difference between the experimental normalized Phase III slope value and the calculated or computed normalized Phase III slope values for each of the paired cardiac output and pulmonary arterial blood $CO_2$ concentration values that are projected on the XY plane in the two-dimensional plot, as is shown in FIG. 4B, and "mountain ranges" rising on either side of the "valley" indicating increasing differences between the experimental normalized Phase III slope value and the calculated or computed normalized Phase III slope values as the distance away from the valley is increased. This calculation is preferably carried out using a computer as the means for processing the information as described.

Figure 4A:
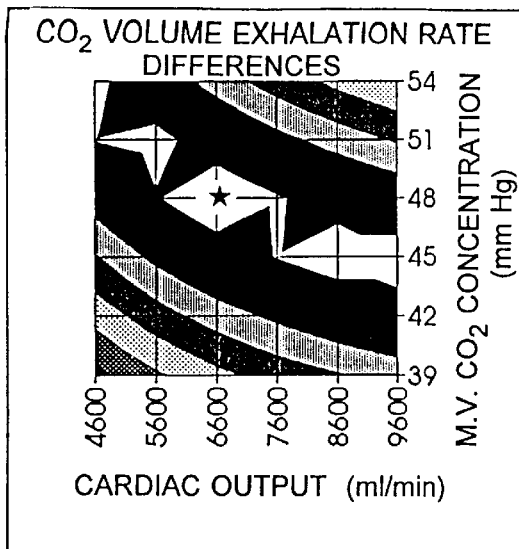
FIGS. 4A and 4B depict contour plots of differences between numerical and experimental parameter values (4A: $CO_2$ volume exhalation rate; 4B: normalized Phase III slope) for paired values of cardiac output and pulmonary arterial (mixed venous) blood $CO_2$ concentration (M.V. $CO_2$ Concentration). The experimental values were parameters for a standard adult male ($\dot{Q}_B$=6600 ml/min; $c_B$=48 mm Hg), and the numerical values were also calculated based on these same parameter values. White areas in the plot indicate small differences between the experimental and calculated values; the shaded contours indicate areas or regions where the differences between the experimental and calculated values became progressively larger as the distance from the white areas (minimal difference) increased. The cardiac output for the standard individual is determined by overlaying the contour plots of FIGS. 4A and 4B, which yields a single point (★) having mutually minimized values of normalized Phase III slope and $CO_2$ volume exhalation rate, where cardiac output=6600 ml/min and pulmonary arterial blood $CO_2$ concentration=48 mm Hg.
Figure 4B:
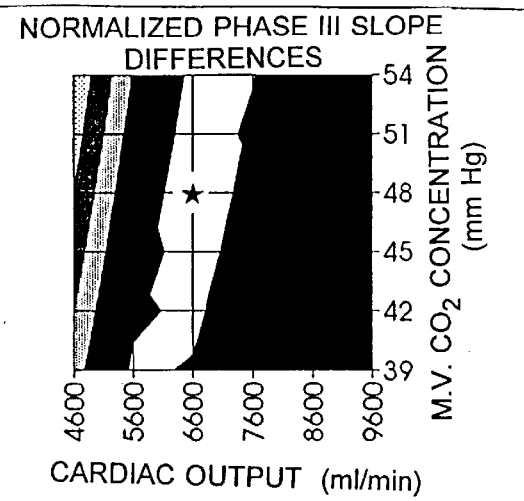
Figure 5A:
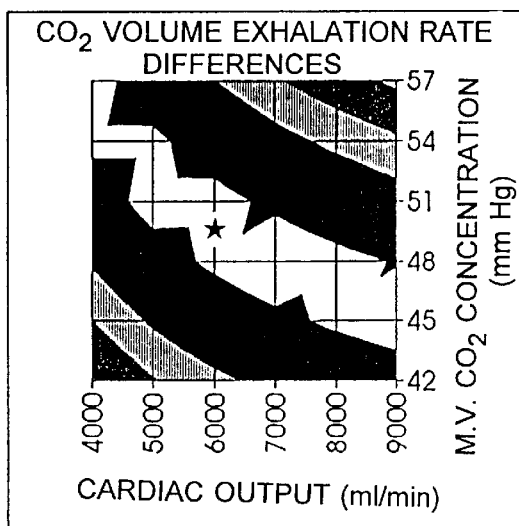
FIGS. 5A and 5B are similar to the contour plots shown in FIGS. 4A and 4B except that the experimental values of $CO_2$ exhalation rate (5A) and normalized Phase III slope (5B) were obtained from a test individual ($\dot{Q}_B$=5820 ml/min; $c_B$=48.6 mm Hg). The cardiac output for the test individual is determined by overlaying the contour plots of FIGS. 5A and 5B, which yields a single point (★) having mutually minimized values of normalized Phase III slope and $CO_2$ volume exhalation rate, where cardiac output=6000 ml/min and pulmonary arterial blood $CO_2$ concentration=49–50 mm Hg.
Figure 5B:
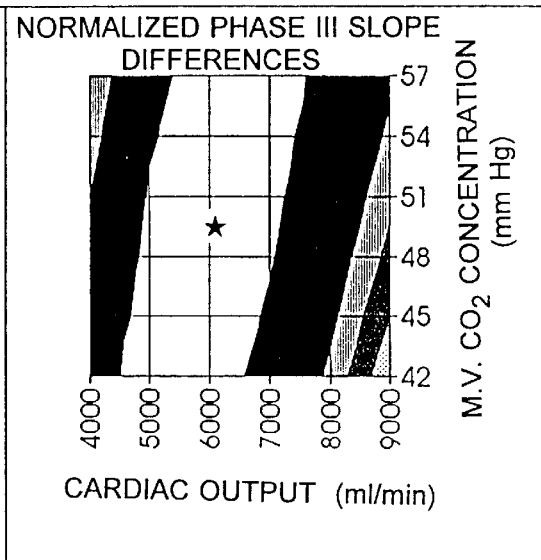

A similar technique may also be used with the difference data generated using the second parameter, $CO_2$ volume exhalation rate, to generate a second contour map, such as shown in FIG. 4A.

Determination of the cardiac output and pulmonary arterial blood $CO_2$ concentration is made by carrying out a cross comparison of the respective regions of minimized differences to determine for which single paired value of cardiac output and pulmonary arterial blood $CO_2$ concentration these two parameters are each minimized. A single value of cardiac output and pulmonary arterial blood $CO_2$ concentration may be determined, according to this invention, since it has been discovered that the respective regions of minimized differences for each of the two parameters are generally longitudinal in shape, i.e., "valleys", that unexpectedly are oriented in an orthogonal or perpendicular relationship to each other, when compared as a function of cardiac output and pulmonary arterial blood $CO_2$ concentration. This relationship is more easily understood by reference to the Figures, particularly FIGS. 4A and 4B, 5A and 5B, and 8A and 8B. If any of these paired plots of A and B are overlaid, with the cardiac output (X axis) and pulmonary arterial blood $CO_2$ concentration (Y axis) aligned so that identical values of these parameters on the A and B plots are likewise aligned, a single value of cardiac output and pulmonary arterial blood $CO_2$ concentration may be identified at the point of mutually minimized differences. This point (★) is noted on each of the Figures, and is the value of cardiac output and of pulmonary arterial blood $CO_2$ concentration determined noninvasively by this invention for the respective test individuals whose data are plotted in the Figures.

Other approaches for cross-comparing the paired experimental and calculated values of cardiac output and of pulmonary arterial blood $CO_2$ concentration may also be used to determine the value of cardiac output and of pulmonary arterial blood $CO_2$ concentration most representative of the test individual, and these will be evident to those skilled in the art based on the disclosures in this specification. For example, the cross-comparison may be based on comparison of the multiplication products of the paired experimental and calculated difference values, rather than the two difference values separately. Likewise, mathematical techniques exist that allow interpolation or extrapolation of the value of cardiac output and of pulmonary arterial blood $CO_2$ concentration most representative of the test individual from a small sampling of data set values, avoiding the need to compare each and every paired value in the experimental and calculated data sets. These and other similar alternative approaches are also within the scope of the present invention.

The methodology described above utilizes paired values of cardiac output and of pulmonary arterial blood $CO_2$ concentration that are developed using a single-path model of airway convection and diffusion. Based on the disclosures in this specification, it should be evident to one skilled in the art that the methodology used in this invention is likewise applicable to other alternative models, e.g., a multiple path model based on a plurality of single path models.

In a preferred aspect of the present invention, a database is created containing a population of computed numerical $CO_2$ expirograms with associated paired numerical normalized Phase III slope and $CO_2$ volume exhalation rate values for a range of assumed value for cardiac output and for pulmonary arterial blood $CO_2$ concentration with ranges that overlap the expected cardiac output and pulmonary arterial blood $CO_2$ concentration of the test individual or individuals. This population of computed numerical $CO_2$ expirograms also is generated for a range of numerical airway area reduction factors that overlaps the expected airway area reduction factor derived from the multiple $CO_2$ expirograms of the test individual or individuals and, furthermore, with a range of assumed values for tidal volume and breathing frequency values that overlap the expected tidal volumes and breathing frequencies used with the test individual or individuals to generate the experimental $CO_2$ expirograms. The population of computed numerical $CO_2$ expirograms is generated using the single-path model as described previously and is readily accomplished by means of a computer.

The generation of this population of computed numerical $CO_2$ expirograms for the database involves a large number of computationally intensive simulations using the single-path model, so it is advantageous to carry out this step prior to obtaining the experimental $CO_2$ expirograms from a test individual. The existence of this information in a precomputed database makes the determination of cardiac output of a test individual by the noninvasive method of the present invention relatively efficient and one that can be accomplished in real time, i.e., the cardiac output and, optionally, pulmonary arterial blood $CO_2$ concentration may be determined for a test individual virtually immediately after the multiple $CO_2$ expirograms are obtained from the test individual, since computational analysis of such data would be relatively instantaneous using commercially available personal computers. Such a database could be stored on the hard drive of a computer or on a CD-ROM storage device or possibly on a set of memory chips, depending on the desired degree of resolution sought for determination of cardiac output.

The present invention also includes an apparatus comprising the database as described above, a device for obtaining a $CO_2$ expirogram from a test individual under steady-state non-rebreathing conditions and a computational means for processing the experimental $CO_2$ expirogram data obtained from the test individual and for executing the computational steps involved in the method of the present invention utilizing the information in the database.

The noninvasive method and apparatus of this invention for determining cardiac output and, optionally and preferably, pulmonary arterial blood $CO_2$ concentration for an individual are particularly advantageous because minimal cooperation is required of the test individual and the procedure is totally noninvasive. The method and apparatus of this invention for determining cardiac output may thus be used with sleeping or anesthetized patients and with individuals for whom full cooperation in breathing maneuvers would present problems, e.g., very young children or critically ill patients. A further advantage of the method and apparatus of the present invention is that the cardiac output determination may be made utilizing hardware elements that are presently commercially available at a reasonable cost. The potential application for a simple, reliable, inexpensive and noninvasive method for determining cardiac output such as is accomplished by the method and apparatus of this invention are quite large and range from use in critical care patient monitoring to routine physical examinations to use as a diagnostic aid in personal or recreational exercise equipment.

The present invention is illustrated further by the following nonlimiting Example.

EXAMPLE

This Example describes the noninvasive determination of cardiac output and pulmonary arterial blood $CO_2$ concentration according to this invention in a study that also obtained, by invasive methods, information about the test individuals' cardiac output and mixed venous blood $CO_2$ concentration for comparison with the noninvasively determined parameter values.

The study described below was approved by the Human Studies Subcommittee of the Philadelphia VA Medical Center. Four healthy human adult male volunteers were recruited from the Faculty of Anesthesia at the University of Pennsylvania. Each individual reclined on a litter while a 20-gauge arterial cannula was inserted into the left radial artery and a long line CVP (central venous pressure) drum catheter, (Abbott Laboratories, Chicago, Ill.) was placed in an antecubital vein and advanced into the central venous circulation. Position of the CVP catheter was deemed optimal if the pressure trace showed clear respiratory artifact with spontaneous breathing in the absence of ventricular extrasystoles and venous blood could be aspirated without difficulty. Arterial and central venous pressures were continuously monitored using standard pressure transducers along with the electrocardiogram. After placement of the monitoring lines, the individual was seated on a bicycle ergometer which was adjusted to the individual. During the measurement period at each exercise level, blood samples were drawn simultaneously from the arterial and central venous cannulae for blood gas determinations while the breath-by-breath $CO_2$ data were collected.

Figure 2:
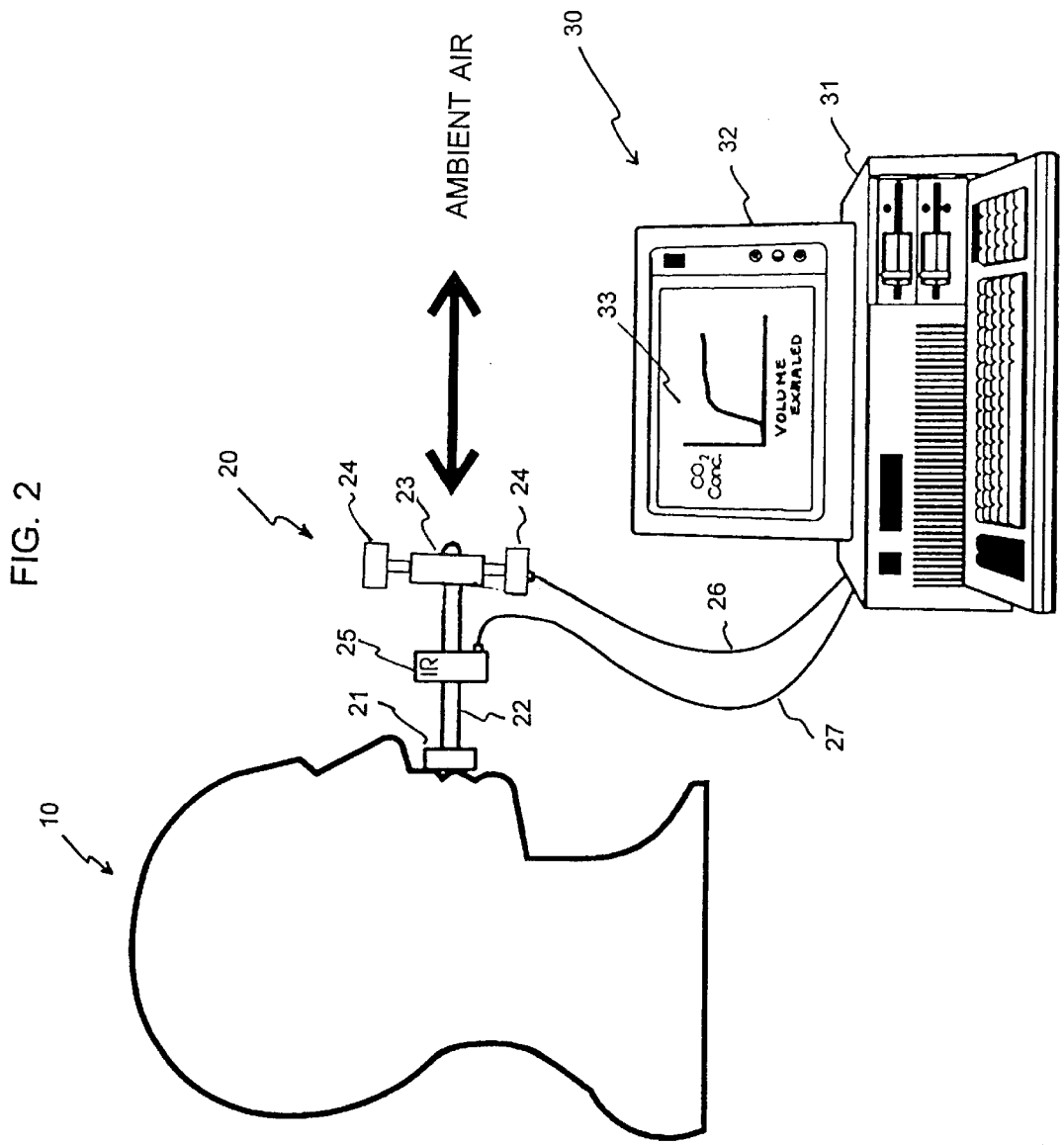
FIG. 2 is a schematic diagram showing the hardware used to collect $CO_2$ expirogram (washout) data from a test individual (head silhouette), infrared $CO_2$ and gas flow transducers and a PC-type computer for processing the collected data and reporting the determined results.

The equipment for obtaining and processing $CO_2$ expirograms from the test individuals is shown schematically in FIG. 2, where the head silhouette 10 represents a test individual, the device 20 obtains the raw $CO_2$ expirogram data and a computer 30 is the means used to process the $CO_2$ expirogram data to determine noninvasively the cardiac output and pulmonary arterial blood $CO_2$ concentration for the test individual.

The experimental exercise protocol consisted of collecting two sets of 15 washout curves, i.e., $CO_2$ expirograms, at base line, light exercise, moderate exercise, and again at base line conditions. Between each pair of measurement sets, blood gases and cardiac output (in duplicate) were measured by indicator dilution. As shown in part in FIG. 2, all test individuals were seated and breathed ambient air through a mouthpiece 21 (with a noseclip (not shown)) connected by a tube 22 to a non-rebreathing valve 23 that enabled the individuals to breathe ambient air. The $CO_2$ washout data were collected using an infrared $CO_2$ analyzer 25 (Novametrics Model 1260) and heated pneumotachometers 24 (Hans-Rudolph, Inc., Kansas City, Mo., Model 3813), and these transducers were connected to a computer 30.

For light exercise conditions, these individuals slowly pedaled the exercise bicycle ergometer; for moderate exercise conditions, the individuals pedaled at a faster rate to achieve a target heart rate. The heart rate target ranges were 60–75 beats per minute, 90–95 beats per minute, and 110–120 beats per minute for rest, light exercise and moderate exercise, respectively. At each level of exercise, steady-state was achieved by monitoring breath by the breath parameter, $CO_2$ volume exhalation rate.

As shown in FIG. 2, the data from the single-breath $CO_2$ washout measurements consisted of analog data from the infrared $CO_2$ analyzer 25 and the pneumotachometers 24 that were collected in analog form, transmitted by lines 27 and 26 to a computer 30, where the data passed through an analog-to-digital converter (Metrabyte DAS8, Keithley Metrabyte, Taunton, Mass.) and was processed in an IBM-compatible PC-type computer 31 (386DX). Processed $CO_2$ expirogram information could be viewed in graphical or plotted form 33 on the computer monitor 32, as shown in FIG. 2.

After each set of 15 breaths obtained from a test individual, cardiac output was experimentally measured by invasive indicator dilution, using a 4 to 10 mg injection of indocyanine green, while continuously sampling arterial blood through a dye dilution densitometer; see Schreiner et al., *J. Clin. Monit.* 5:236–242 (1989).

The noninvasive instrumentation and instrumentation procedures used in this study are described in more detail in Neufeld et al., "Diffusivity, Respiratory Rate and Tidal Volume Influence Inert Gas Expirograms," *Respir. Physiol.*, 84:31–47 (1991). The pneumotachometer data consisted of gas flow rate data.

For each of the $CO_2$ washout curves, i.e., $CO_2$ expirograms, the computer was programmed to calculate, as described above, a normalized Phase III slope and a $CO_2$ volume exhalation rate as experimentally measured values of these two parameters.

For individual $CO_2$ expirograms obtained in this study, the normalized Phase III slopes as a function of tidal volumes were generated, and these data were used as the basis for determining a value of the airway area reduction factor β that best characterized the data for a given test individual. This is shown in FIG. 3, where normalized Phase III slope versus tidal volume (normalized to the test individual's body weight) data for numerous $CO_2$ expirograms are plotted for expirograms obtained for one test individual at the breathing protocols used: initial at rest baseline (Base 1 in FIG. 3) and final at rest baseline (Base 2 in FIG. 3) and for light exercise and moderate exercise. The plot shown in FIG. 3 also shows reference curves for several values of the airway area reduction factor $\beta$, ranging from 0.5 to 1, and these curves were generated using the single-path model with standard values for cardiac output (6600 ml/min) and pulmonary artery $CO_2$ concentration (48 mm Hg), since $\beta$ is generally insensitive to these two parameters. The value of $\beta$ that is characteristic of the plotted data for a given test individual may be derived by matching the test individual's experimental normalized Phase III slope data (as a function of tidal volume) to the results of the single-path model computed simulations at equivalent tidal volumes. The resulting characteristic $\beta$ factor for a test individual is then used in the single-path model simulations of $CO_2$ expirograms used to generate computed values of normalized Phase III slope and $CO_2$ volume exhalation rate values.

As is shown by the data plotted in FIG. 3, a closer or better fit of the data is obtained at the higher tidal volumes, e.g., above about 15 ml/kg, so it is preferable to select the individual $CO_2$ expirogram (or averaged expirograms) used in the comparison of numerical vs. experimental parameters from among expirograms in this region.

The contour maps shown for the normalized Phase III slope differences and for the $CO_2$ exhalation rate differences as a function of cardiac output ($\dot{Q}_B$) and of pulmonary arterial blood $CO_2$ concentration ($c_B$) were generated by running the single-path model at the 36 different grid points shown on the respective plots and interpolating on a linear basis the remaining data point regions of the grid. It should be noted that the computations required to generate such contour maps are time-consuming, since the single-path model should be run to steady-state (about 6 breaths) for each point; for example, such a computation on a Sparcstation #10 requires about 5 CPU (computer processing units) minutes. To insure that the experimental value of cardiac output and pulmonary arterial blood $CO_2$ concentration for the test individual fall within the ranges selected for these two parameters, such parameter ranges should be fairly wide to insure that the experimental values of the two parameters for the test individual fall within the selected range and are thus bracketed by difference data. Such wide parameter ranges, however, require generation of a relatively large information database, and this is one reason why generation of a data base with assumed values is desirably carried out in advance of the time at which experimental $CO_2$ expirogram data are obtained from a test individual and processed according to the present method. An alternative to the creation of an information database is the use of a computational shortcut for systematically searching through the different data to determine the point at which such differences are minimized. One such computational shortcut is via use of the simplex algorithm; see, e.g., Reklaitis et al., "Engineering Optimization," Wiley & Company, New York (1993).

Cardiac output values determined from selected individual breath $CO_2$ expirograms of the test individuals in this study are illustrated in FIGS. 6A (individual $CO_2$ expirograms) and 6B (averaged breath $CO_2$ expirograms), which are plots comparing cardiac outputs determined noninvasively by the inventive method ("noninvasive cardiac output") and cardiac outputs determined by the invasive technique ("invasive cardiac output"). A regression analysis of the data in FIG. 6A forced through 0 yielded Y=1.09 x, R=0.828 and S.E.E. (standard error of estimate) y=0.405. Most of the outlying points among the data shown in FIG. 6A correspond to test individual #2 for whom difficulties were present during the indicator dilution measurements (in blood sampling) that were not encountered with the other test individuals. If the data for test individual #2 are deleted and a regression analysis performed on the remaining data shown in FIG. 6A, the result is y=1.05 x, R=0.853, and S.E.E. y=0.0371. An alternative procedure in which the breaths were averaged prior to determining the cardiac output did not significantly improve the results, and these data are shown in FIG. 6B.

Mixed venous blood $CO_2$ concentrations determined from selected individual breath $CO_2$ expirograms of the test individuals in this study are illustrated in FIGS. 7A (individual $CO_2$ expirograms) and 7B (averaged breath $CO_2$ expirograms), which are plots comparing mixed venous blood $CO_2$ concentrations determined noninvasively by the inventive method ("noninvasive $c_B$") and cardiac outputs determined by the invasive technique ("invasive $c_B$"). The experimental data show that mixed venous blood $CO_2$ concentration rose, as would be expected, with exercise only for test individual #2. However, all of the corresponding values of mixed venous blood $CO_2$ concentration determined noninvasively from the single-path model calculations show an increase with exercise. Invasively-determined data for test individuals #3 and #4 remained essentially unchanged through all of the exercise stages. The mixed venous blood $CO_2$ concentrations calculated for these two individuals were closest to their counterpart invasively-determined values only during the base line protocol with the test individuals at rest. These results suggest that the central venous catheter may not have been positioned adequately to sample a true mixed venous blood in the invasive procedure and thereby provide an accurate value for mixed venous blood $CO_2$ concentration. It should also be noted that a more preferred procedure, but one carrying a higher risk, would have involved sampling right side pulmonary arterial blood, which is more likely to provide an accurate measurement of pulmonary arterial blood $CO_2$ concentration since such blood is likely to be better mixed than that obtained by sampling in this study.

Indicator dilution measurements of cardiac output are generally regarded as having errors of plus or minus 15%. In this study, all breathing measurements and blood gas samples were collected during a steady-state exercise level, after which indicator dilution measurements were taken. Since the data were not collected concurrently for all measurements, variations in actual blood flow during the measurements could account for experimental variation in the data obtained in this study. The standard error of the estimate (S.E.E.) for the data was 0.0405 (including test individual #2) and was 0.0371 (excluding test individual #2). In both cases, the results demonstrate that the noninvasive method for determining cardiac output utilized in this study is capable of determining cardiac output values for the test individuals.

The results for values of mixed venous blood $CO_2$ concentration did not show a good correlation between values calculated noninvasively from the $CO_2$ expirogram data, but this may be a consequence of a blood sampling technique that failed to provide accurate values of mixed venous blood $CO_2$ concentration in the test individuals. As noted earlier, a central venous cannulation procedure was used for blood sampling in this study but pulmonary artery catheterization is preferred for determining accurately the actual mixed venous blood data. In any event, the values of this parameter calculated noninvasively from the single-path model indicated changes in mixed venous blood $CO_2$ concentration that were appropriate for the exercise level being evaluated.

In the average data and in the experimental measurements of cardiac output by dilution, it was assumed that cardiac output for the test individual and pulmonary arterial blood $CO_2$ concentration for the test individual remained constant during the time that the $CO_2$ washout was measured, a duration of 15 breaths for approximately 45–90 seconds. Since the test individuals were allowed to reach steady-state breathing naturally, either at rest or during the exercise conditions, it is a reasonable assumption that relatively constant values for these parameters were achieved. In this respect, the method utilized in this study is superior to inert gas rebreathing techniques, since rebreathing ones own carbon dioxide increases the pulmonary arterial blood $CO_2$ concentration, which tends to increase the heart rate and cardiac output during the course of the measurements being made.

Figure 8A:
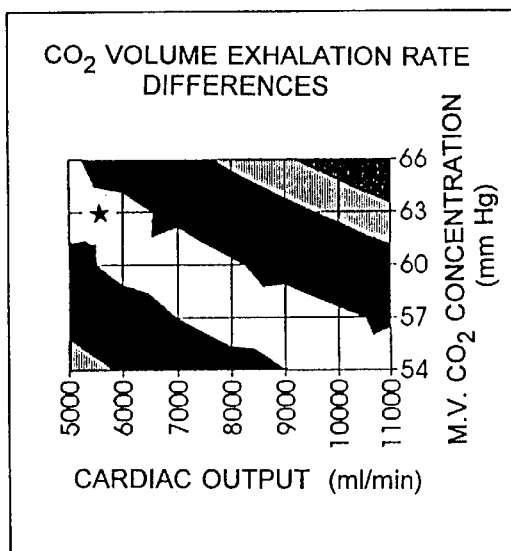
FIGS. 8A and 8B are similar to FIGS. 5A and 5B except that the test individual was a patient exhibiting chronic obstructive pulmonary disease and having an airway area reduction factor β equal to 0.52. The cardiac output for the test individual is determined by overlaying the contour plots of FIGS. 8A and 8B, which yields a single point (★) having mutually minimized values of normalized Phase III slope and $CO_2$ volume exhalation rate, where cardiac output=5500 ml/min and pulmonary arterial blood $CO_2$ concentration=63 mm Hg.
Figure 8B:
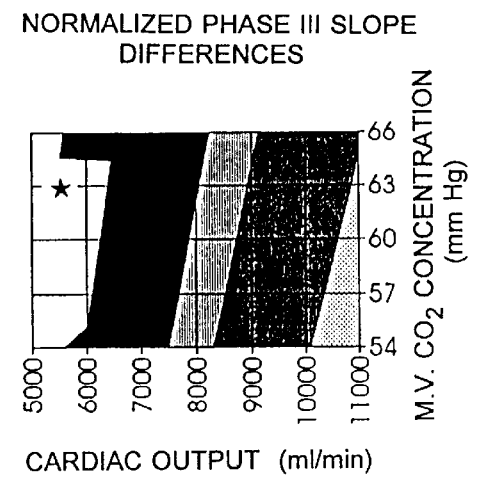

In the present study, cardiac output was determined in a population of healthy adults as test individuals. The method of noninvasively determining cardiac output as described herein may also be used to determined cardiac output in other individuals who do not fit into this category, e.g., children or individuals suffering from lung disease. With suitable adjustments in the selection of the anatomical human lung model used in the single-path mathematical model, the present method can readily provide cardiac output determinations and pulmonary arterial blood $CO_2$ concentration determinations for such individuals. For example, Ream et al., in "Volumetric Capnography in Children," *Anesthesiology*, 82:64–73 (1995) describe the creation of a series of morphometric pediatric lung models for use in a single-path numerical model which provided simulated carbon dioxide washout data that closely matched the experimental data collected in children. Likewise, Schwardt et al., "Noninvasive Recovery of Acinar Anatomic Information from $CO_2$ Expirograms," *Ann. Biomed. Eng.*, 22:293–306 (1994) adapted the morphometric models of Weibel Model A and Hansen and Ampaya in the single-path model to provide numerical $CO_2$ expirogram data that correlate well with experimental values obtained from patients suffering from emphysema. The data presented in the Schwardt et al. paper were utilized in the method of this invention to generate the contour maps shown in FIGS. 8A and 8B that provide cardiac output and pulmonary arterial blood $CO_2$ concentration values for a test individual suffering from chronic obstructive pulmonary disease. The results shown in FIGS. 8A and 8B show that cardiac output for such a test individual is normal compared to that of a healthy adult individual but pulmonary arterial blood $CO_2$ concentration is much higher, as expected in such individuals.

The present invention may be embodied in other specific forms without departing from the spirit or essential attributes thereof and, accordingly, reference should be made to the appended claims, rather than to the foregoing specification, as indicating the scope of the invention.

We claim:

1. A noninvasive method for determining cardiac output for an individual which comprises (i) obtaining a data set of multiple $CO_2$ expirograms from a test individual;

(ii) determining an airway factor for the data set of multiple $CO_2$ expirograms, to obtain an airway factor characteristic of the test individual;

(iii) generating a database of computed numerical $CO_2$ expirograms from an airway numerical model using the airway factor that is characteristic of the test individual and using a range of assumed numerical values for cardiac output that overlaps the expected cardiac output of the test individual;

(iv) comparing differences between numerical values of a $CO_2$ expirogram first parameter and an experimental counterpart parameter value from a $CO_2$ expirogram of the test individual and determining, as a function of the numerical cardiac output values, for which cardiac output values such differences are minimized;

(v) comparing differences between numerical values of a $CO_2$ expirogram second parameter and an experimental counterpart parameter value from a $CO_2$ expirogram of the test individual and determining, as a function of the numerical cardiac output values, for which cardiac output values such differences are minimized; and (vi) determining a cardiac output for the test individual by cross-comparing the information from (iv) and (v) to obtain a cardiac output value at which the respective differences for the $CO_2$ expirogram first parameter and for the $CO_2$ expirogram second parameter are each minimized, said value being the cardiac output noninvasively determined for the test individual.

2. The method of claim 1 which comprises carrying out step (iii) in advance of step (i), to create a database of computed numerical $CO_2$ expirograms that includes ranges of parameter values that overlap the expected values of such parameters for a population of individuals that includes the test individual.

3. A noninvasive method for determining cardiac output ($\dot{Q}_B$) for an individual which comprises (i) obtaining multiple $CO_2$ expirograms from a test individual wherein such expirograms include Phase III data;

(ii) calculating a normalized Phase III slope, NS, as a function of tidal volume for individual $CO_2$ expirograms obtained from the test individual, to generate a population of experimental paired values of normalized Phase III slope as function of tidal volume for such $CO_2$ expirograms;

(iii) determining an airway area reduction factor for the population of experimental paired values of normalized slope and tidal volume, to obtain an airway area reduction factor characteristic of the test individual;

(iv) generating a population of computed numerical $CO_2$ expirograms with associated paired numerical normalized Phase III slope and $CO_2$ volume exhalation rate values, from an airway numerical model using the airway area reduction factor that is characteristic of the test individual and using a range of assumed numerical values for cardiac output, $\dot{Q}_B$, and pulmonary arterial blood $CO_2$ concentration, $c_B$, with ranges that overlap the expected $\dot{Q}_B$ and $c_B$ of the test individual;

(v) comparing the differences between numerical normalized Phase III slope values and an experimental normalized Phase III slope value from a $CO_2$ expirogram of the test individual and determining, as a function of the numerical $\dot{Q}_B$ and $c_B$ values, for which paired $\dot{Q}_B$ and $c_B$ values such differences are minimized;

(vi) comparing the differences between numerical $CO_2$ volume exhalation rate values and an experimental $CO_2$ volume exhalation rate value from a $CO_2$ expirogram of the test individual and determining, as a function of the numerical $\dot{Q}_B$ and $c_B$ values, for which paired $\dot{Q}_B$ and $c_B$ values such differences are minimized; and (vii) determining a cardiac output for the test individual by cross-comparing the information from (v) and (vi) to obtain a paired value of $\dot{Q}_B$ and $c_B$ at which the respective differences of both normalized Phase III slope and $CO_2$ volume exhalation rate are minimized, the value of cardiac output in said paired value being the cardiac output determined for the test individual.

4. The method of claim 3 wherein the $CO_2$ expirograms of step (i) are steady-state single breath $CO_2$ expirograms of the test individual breathing ambient air.

5. The method of claim 3 wherein the $CO_2$ expirograms of step (i) are steady-state non-rebreathing $CO_2$ expirograms of the test individual breathing ambient air.

6. The method of claim 3 wherein the $CO_2$ expirograms are obtained from the test individual under breathing conditions selected from the group consisting of normal breathing, shallow breathing, rapid breathing, rapid-shallow breathing, slow breathing, deep breathing, and slow-deep breathing.

7. The method of claim 3 wherein at least ten $CO_2$ expirograms are obtained from the test individual.

8. The method of claim 3 wherein the $CO_2$ expirograms are obtained from the test individual under conditions selected from the group consisting of resting, light exercise, moderate exercise, heavy exercise, sleeping, mechanically ventilated, anesthetized and unconscious.

9. The method of claim 3 wherein the airway numerical model is a single-path airway model.

10. The method of claim 9 wherein the single-path airway model utilizes a morphometric lung model selected from the group consisting of Weibel Model A, Hansen & Ampaya, and Haefeli-Bleuer & Weibel.

11. The method of claim 3 wherein the assumed values of $\dot{Q}_B$ used in step (iv) are within the range of from about 1 to about 20 l/min.

12. The method of claim 3 wherein the assumed values of $c_B$ used in step (iv) are within the range of from about 30 to about 80 mm Hg.

13. The method of claim 3 which comprises carrying out step (iv) in advance of step (i), to create a database of computed numerical $CO_2$ expirograms that includes ranges of values of airway area reduction factor, tidal volume, breathing frequency, cardiac output and pulmonary arterial blood $CO_2$ concentration that overlap the expected values of such parameters for a population of individuals that includes the test individual.

14. The method of claim 13 wherein, in step (iv), the airway area reduction factor ranges from about 0.2 to about 2.

15. The method of claim 13 wherein, in step (iv), the tidal volume ranges from about 200 to about 2500 ml.

16. The method of claim 13 wherein, in step (iv), the breathing frequency ranges from about 4 to about 40 breaths per minute.

17. The method of claim 3 wherein the comparison of differences between numerical values and an experimental value is carried out with said values being obtained from $CO_2$ expirograms at equivalent tidal volumes and breathing frequencies.

18. The method of claim 3 wherein the same $CO_2$ expirogram of the test individual is used in steps (v) and (vi).

19. The method of claim 3 wherein the $CO_2$ expirogram of the test individual used in steps (v) and (vi) is an average of two or more $CO_2$ expirograms of the test individual.

20. The method of claim 3 wherein the $CO_2$ expirogram of the test individual used in steps (v) and (vi) is a $CO_2$ expirogram obtained from the individual at rest and breathing normally.

21. The method of claim 3 which further comprises repeating steps (v) and (vii) with a different $CO_2$ expirogram from the test individual to obtain multiple values of cardiac output for the test individual and then selecting a single value or averaged value of cardiac output as the cardiac output representative of such test individual.

22. The method of claim 3 which further comprises determining the pulmonary arterial blood $CO_2$ concentration for the test individual, the paired values of $\dot{Q}_B$ and $c_B$ obtained from the cross-comparison in step (vii) being the cardiac output and pulmonary arterial blood $CO_2$ concentration determined for the test individual.

23. An apparatus for the noninvasive determination of cardiac output for a test individual which comprises (i) a database comprising a population of computed numerical $CO_2$ expirograms for a range of assumed parameter values, including cardiac output, that overlap expected values of these parameters in a population of individuals that includes the test individual;

(ii) a device for measuring $CO_2$ gas expirogram data from the test individual;

(iii) means for processing data from multiple $CO_2$ expirograms obtained from the test individual to generate a $CO_2$ expirogram data set for the test individual and for calculating an airway factor characteristic of the test individual from such multiple $CO_2$ expirogram data set;

(iv) means for computing differences between an experimental value of a first parameter from a $CO_2$ expirogram of the test individual and computed values of the first parameter from numerical $CO_2$ expirograms in the database, whose assumed airway factor is comparable to that of the experimental $CO_2$ expirogram, and for determining for which values of cardiac output such differences are minimized;

(v) means for computing differences between an experimental value of a second parameter from a $CO_2$ expirogram of the test individual and computed values of the second parameter values from numerical $CO_2$ expirograms in the database, whose assumed airway factor is comparable to that of the experimental $CO_2$ expirogram, and for determining for which values of cardiac output such differences are minimized;

(vi) means for determining a cardiac output for the test individual by cross-comparing the information from (iv) and (v) to obtain a value of cardiac output at which the respective differences of the $CO_2$ expirogram first parameter and the $CO_2$ expirogram second parameter are each minimized; and (vii) means for reporting the value of cardiac output determined in (vi) as the cardiac output of the test individual.

24. The apparatus of claim 23 wherein the means for processing the data from the $CO_2$ expirograms in (iii) is a computer.

25. The apparatus of claim 23 wherein the means for computing the differences between experimental and numerical values in (iv) and (v) and the means for cross-comparing the information in (vi) is a computer.

26. An apparatus for the noninvasive determination of cardiac output for a test individual which comprises (i) a database comprising a population of computed numerical $CO_2$ expirograms for a range of assumed values for cardiac output, pulmonary arterial blood $CO_2$ concentration, airway area reduction factor, tidal volume and breathing frequency that overlap expected values of these parameters in a population of individuals that includes the test individual;

(ii) a device for measuring $CO_2$ gas concentration, gas volume, breathing frequency and tidal volume for single breaths from the test individual under steady-state non-rebreathing conditions to generate $CO_2$ expirogram data for the test individual;

(iii) means for processing data from multiple $CO_2$ expirograms obtained from the test individual to calculate a normalized Phase III slope and tidal volume for each of said multiple $CO_2$ expirograms and to calculate an airway area reduction factor characteristic of the test individual from such multiple $CO_2$ expirogram data;

(iv) means for computing differences between an experimental normalized Phase III slope from a $CO_2$ expirogram of the test individual and computed values of experimental normalized Phase III slopes in the database, for numerical $CO_2$ expirograms whose assumed airway area reduction factor, tidal volume and breathing frequency are comparable to that of the experimental $CO_2$ expirogram, and for determining for which values of cardiac output and pulmonary arterial blood $CO_2$ concentration such differences are minimized;

(v) means for computing differences between an experimental $CO_2$ volume exhalation rate from a $CO_2$ expirogram of the test individual and computed values of experimental $CO_2$ volume exhalation rate values in the database, for numerical $CO_2$ expirograms whose assumed airway area reduction factor, tidal volume and breathing frequency are comparable to that of the experimental $CO_2$ expirogram, and for determining for which values of cardiac output and pulmonary arterial blood $CO_2$ concentration such differences are minimized;

(vi) means for determining a cardiac output for the test individual by cross-comparing the information from (iv) and (v) to obtain paired values of cardiac output and pulmonary arterial blood $CO_2$ concentration at which the respective differences of both normalized Phase III slope and $CO_2$ volume exhalation rate are minimized; and (vii) means for reporting the value of cardiac output determined in (vi) as the cardiac output of the test individual.

27. The apparatus of claim 26 wherein the means for processing the data from the multiple $CO_2$ expirograms is a computer.

28. The apparatus of claim 26 wherein the means for computing the differences between experimental and numerical values in (iv) and (v) and the means for cross-comparing the information in (vi) is a computer.

* * * * *